United States Patent [19]

Johnsen et al.

[11] Patent Number: 5,316,607
[45] Date of Patent: May 31, 1994

[54] METHOD FOR FABRICATING AN OSTOMY DEVICE WITH A CONVEX ADHESIVE FACEPLATE AND PROTECTIVE SHIELD

[75] Inventors: Kenneth A. Johnsen, Piscataway; Keith T. Ferguson, Scotch Plains, both of N.J.

[73] Assignee: E. R. Squibb & Sons, Princeton, N.J.

[21] Appl. No.: 846,783

[22] Filed: Mar. 4, 1992

Related U.S. Application Data

[60] Division of Ser. No. 723,467, Jun. 28, 1991, abandoned, which is a continuation of Ser. No. 399,829, Aug. 28, 1989, abandoned.

[51] Int. Cl.$^5$ .............................................. B32B 31/00
[52] U.S. Cl. ..................... 156/212; 156/285; 156/286; 156/382
[58] Field of Search ............... 156/285, 286, 313, 381, 156/382, 212, 321, 322; 604/332, 338, 339, 344, 345; 264/510, 548

[56] References Cited

U.S. PATENT DOCUMENTS

| | | | |
|---|---|---|---|
| 2,828,799 | 4/1958 | Harrison, Jr. ...................... | 156/286 |
| 2,978,376 | 4/1961 | Hulse ................................... | 156/286 |
| 4,710,182 | 12/1987 | Bryson ................................ | 604/339 |
| 4,769,100 | 9/1988 | Short et al. ........................ | 156/286 |
| 4,834,731 | 5/1989 | Nowak et al. ..................... | 604/339 |

*Primary Examiner*—Geoffrey L. Knable
*Assistant Examiner*—Richard Crispino
*Attorney, Agent, or Firm*—James & Franklin

[57] ABSTRACT

A plastic annular disk has a convex exterior surface upon which is situated an adhesive wafer. A removable protective shield is formed to have a substantially wrinkle-free surface with a contour identical to that of the convex surface. The disk and wafer are placed in a vacuum chamber, below a planar plastic sheet. The top of the chamber is heated. The space above the sheet is evacuated to draw the sheet against the heated surface. The remaining portion of the chamber is then evacuated to eliminate air between the wafer and disk. Lastly, the top of the chamber is vented such that the heated sheet is pressed over the wafer and disk.

8 Claims, 9 Drawing Sheets

METHOD FOR FABRICATING AN OSTOMY DEVICE WITH A CONVEX ADHESIVE FACEPLATE AND PROTECTIVE SHIELD

This is a divisional of co-pending application Ser. No. 723,467, filed Jun. 28, 1991, now abandoned which is a continuation of application Ser. No. 399,829, filed Aug. 28, 1989, now abandoned.

The present invention relates to ostomy devices of the type including a waste collection pouch which is affixed to the skin surrounding the stoma by means of an adhesive coated faceplate and more particularly to such a device which includes a convex adhesive faceplate designed for use with patients having specialized problems and a method for fabricating same.

BACKGROUND OF THE INVENTION

Certain surgical procedures known as colostomy, ileostomy and urostomy result in an opening in the abdominal wall, called a stoma, which permits waste discharge from the interior of a body cavity. Since the patient has no control over the waste discharge, it is often necessary for the patient to utilize an ostomy device to protect the stoma and collect the waste material as it is discharged.

Over the years, ostomy devices of a variety of different types and constructions have been utilized. Various materials and adhesives have been developed to increase the utility and wearability of same.

The basic device includes a collection receptacle or pouch connected to an adhesive coated faceplate which mounts the pouch to the body. The pouch includes first and second thin film walls which are sealed by heat welding or the like along their periphery. The pouch has an inlet opening designed to be aligned with the stoma. In one piece devices, the pouch is permanently affixed to the adhesive coated faceplate. In two piece devices, the pouch is detachably mounted to the faceplate by coupling rings or the like. In this way, the pouch can be replaced without removal of the faceplate each time.

For the ostomy device to function properly, it is necessary that it make a fluid-tight connection with the peristomal skin to prevent any liquid, solid, semi-solid or gaseous waste from escaping and a weight bearing connection to support the weight of the device. When the muscle beneath the skin surrounding the stoma is smooth and has sufficient rigidity and the stoma protrudes outwardly beyond the skin surface, a planar faceplate will achieve good results. However, when the rigidity of the muscle surrounding the stoma is lacking due to advanced age or abnormal stretching or the peristomal skin is scarred or indented or the stoma does not protrude sufficiently, the planar faceplate is often not adequate.

The advisability of the use of a convex faceplate in such situations has been previously recognized. See, for example, Galindo U.S. Pat. No. 4,219,023, issued Aug. 26, 1980 and entitled Convex Insert And Ostomy Bag Structure, in this regard. We are also aware of an ostomy device which includes a convex pressure ring as disclosed in Nowak U.S. Pat. No. 4,834,731. However, up until now, there has been no effective process for mass producing ostomy devices with convex adhesive faceplates in a manner which prevents localized drying of the adhesive layer. Moreover, there are no products which include a convexly shaped protective shield with a relatively wrinkle-free surface which, when removed, leaves a uniform, uninterrupted adhesive surface which will ensure an excellent seal with the skin.

When a planar annular faceplate is used, it is commonly stamped from a sheet of dough-like material. After it is formed, one side is heat welded to the pouch surrounding the inlet opening. The other surface is coated with a layer of adhesive which may be deposited on the surface itself or which may be on a microporous wafer or label. The exposed surface of the adhesive is then provided with a sheet of planar release paper which protects the adhesive until use.

When the faceplate has a planar surface, the process of placing the adhesive coating thereon and the release paper over the adhesive is relatively straight-forward and results in an adhesive coating which is uniform and smooth. However, the use of a convex faceplate instead of a planar faceplate presents certain complications in the conventional fabrication process due to the fact that the faceplate disk is convex but the release paper is planar. Because the release paper is planar and hence does not readily fit the convex contour of the disk, the adhesive layer may contain air gaps which result in localized drying of the adhesive. Moreover, the release paper may become wrinkled due to its inability to properly conform to the convex surface. When this occurs, the adhesive layer may contain surface ridges instead of being smooth. Hence, it is not possible to mass-produce convex faceplates of acceptable quality.

In order to overcome these difficulties, we have invented a fabrication process which lends itself to mass production and in which a uniform adhesive coating is formed on the convex surface of the faceplate disk. Instead of conventional release paper, a thin plastic protective shield is provided. The shield is fabricated to have a substantially wrinkle-free surface with a contour which is identical to the contour of the convex surface of the disk. All air gaps in the adhesive are eliminated during the fabrication process. Hence, when the shield is removed, the adhesive coating on the convex surface of the faceplate disk is completely smooth and has no dry areas.

It is, therefore, a prime object of the present invention to provide a mass producible ostomy device with a convex adhesive faceplate.

It is an another object of the present to provide an ostomy device with a convex adhesive faceplate in which gaps leading to localized drying of the adhesive have been eliminated.

It is another object of the present invention to provide an ostomy device with a convex faceplate and a convex protective shield.

It is another object of the present invention to provide a method for fabricating an ostomy device with a convex adhesive faceplate disk and a convex protective shield with a wrinkle-free surface.

It is another object of the present invention to provide a method for fabricating an ostomy device with a convex faceplate in which the adhesive layer is uniform, smooth and substantially devoid of gaps.

It is another object of the present invention to provide a method for fabricating an ostomy device with a convex adhesive faceplate which employs vacuum forming techniques to form a convex plastic shield.

It is another object of the invention to provide a method for fabricating an ostomy device with a convex adhesive a faceplate wherein a planar plastic sheet is fabricated into a wrinkle-free convex protective shield.

It is another object of the present invention to provide a method for fabricating an ostomy device with a convex adhesive faceplate wherein the plastic protective shield is vacuum formed to ensure that its contours are substantially identical to the contour of the convex surface of the faceplate.

SUMMARY OF THE INVENTION

In accordance with one aspect of the present invention, a faceplate for an ostomy device of the type including a collection pouch having an inlet is provided. The faceplate comprises an annular disk having a convex surface and a central opening. A substantially uniform layer of adhesive is situated on the convex surface of the disk. A removable plastic shield is provided. The shield is formed to have a substantially wrinkle-free contour substantially identical to the contour of the convex surface of the disk. Means are provided for connecting the pouch to the other surface of the disk such that the pouch inlet aligns with the central opening of the disk.

Preferably, the layer of adhesive is in the form of an adhesive wafer. The wafer is most preferably annular in configuration.

A collar is provided having an adhesive coating. The collar has a larger outer diameter than that of the disk. It is affixed to the rear of the disk, outside the area on the disk where the pouch is affixed. The collar includes a fabric backing and a pressure sensitive adhesive.

Preferably the shield is circular. It has a larger outside diameter than the disk.

The disk is preferably formed of a rigid or semi-rigid plastic material.

The disk has a peripheral section surrounding the convex surface portion. Preferably, the peripheral section is substantially planar.

In one embodiment, the rear pouch wall (the wall having the aperture for the stoma) is connected directly to the other surface of the disk such as by welding or the like. The rear pouch wall is then sealed to the front pouch wall around their periphery to form the completed pouch. In another embodiment, the other surface of the disk is secured such as by a double sided adhesive disk, a hot melt adhesive or heat and pressure to a belt ring sealed to the rear pouch wall around the stomal aperture. In a third embodiment, the pouch is detachably mounted to the other side of the disk by interengaging coupling rings.

In accordance with another aspect of the present invention, a faceplate for an ostomy device of the type including a collection pouch having an inlet is provided. The faceplate comprises an annular disk having a convex surface and a central opening. A layer of adhesive is situated on the convex surface of the disk. Removable plastic shield means are vacuum formed from a substantially planar sheet of material. The sheet is heated and fabricated to have a substantially wrinkle-free surface to maintain the smoothness of the adhesive layer surface. The shield also has a contour substantially identical to the contour of the convex surface such that substantially all gaps between the shield and the disk are eliminated. Means are provided for connecting the pouch to the other surface of the disk such that the pouch inlet aligns with the central opening of the disk.

In accordance with another aspect of the present invention, a method is provided for fabricating the faceplate of an ostomy device of the type including a collection pouch having an inlet. The method includes the steps of forming an annular disk with a central opening. The disk is placed within a vacuum chamber adjacent a wafer of adhesive. A substantially planar sheet of plastic is situated adjacent the wafer separating the chamber into first and second portions. The first portion of the chamber is evacuated to draw the sheet against a chamber surface. The surface of the chamber against which the sheet is drawn is heated to soften the sheet. The second portion of the chamber is evacuated to remove substantially all air between the disk and the sheet. The vacuum in the first portion of the chamber is then released to cause the softened sheet to be pressed towards the disk and form a shield with the substantially wrinkle-free surface having a contour substantially identical to the contour of the disk. Thereafter, the pouch is connected to the other side of the disk such that the pouch inlet aligns with the central opening of the disk.

The disk preferably has a substantially convex surface upon which the wafer of adhesive is situated. The protective shield also has a substantially convex surface.

BRIEF DESCRIPTION OF THE DRAWINGS

To these and such other objects which may hereinafter appear, the present invention relates to a faceplate for an ostomy device, the faceplate including a convex adhesive disk and a protective shield, as well as a method for fabricating same, as set forth in detail in the following specification and recited in the annexed claims, taken together with the accompanying drawings wherein like numerals refer to like parts and in which:

DETAILED DESCRIPTION OF THE INVENTION

Figure 1:
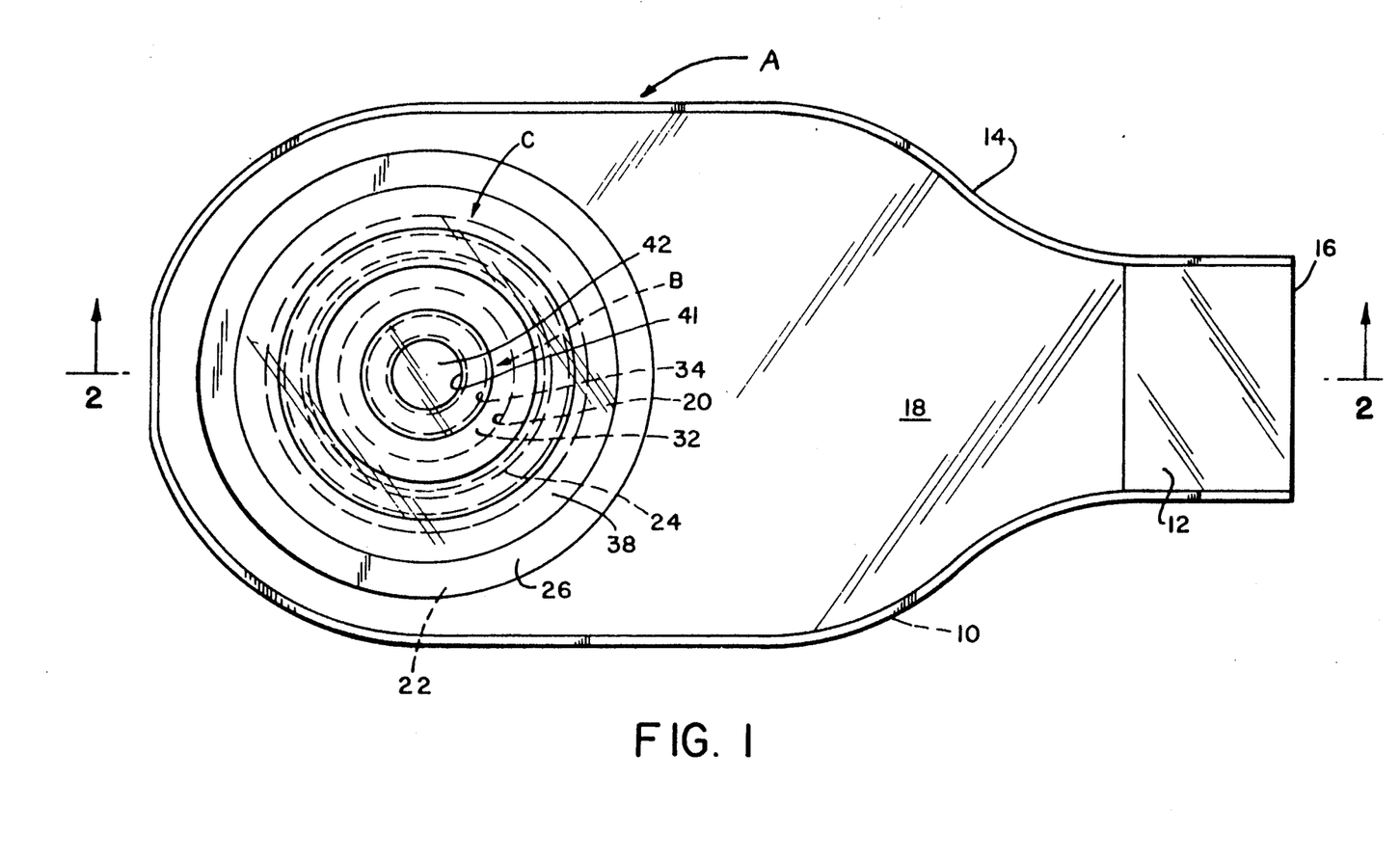
FIG. 1 is an elevational view of the body side of a first preferred embodiment of an ostomy device including the faceplate of the present invention.
Figure 2:
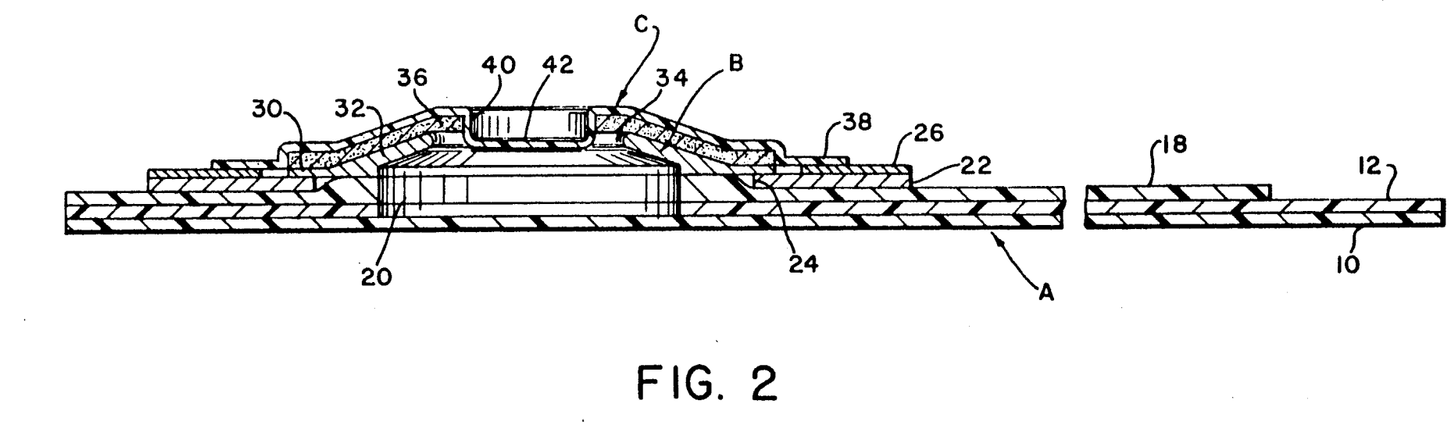
FIG. 2 is a side cross-sectional view taken along line 2—2 of FIG. 1.
Figure 3:
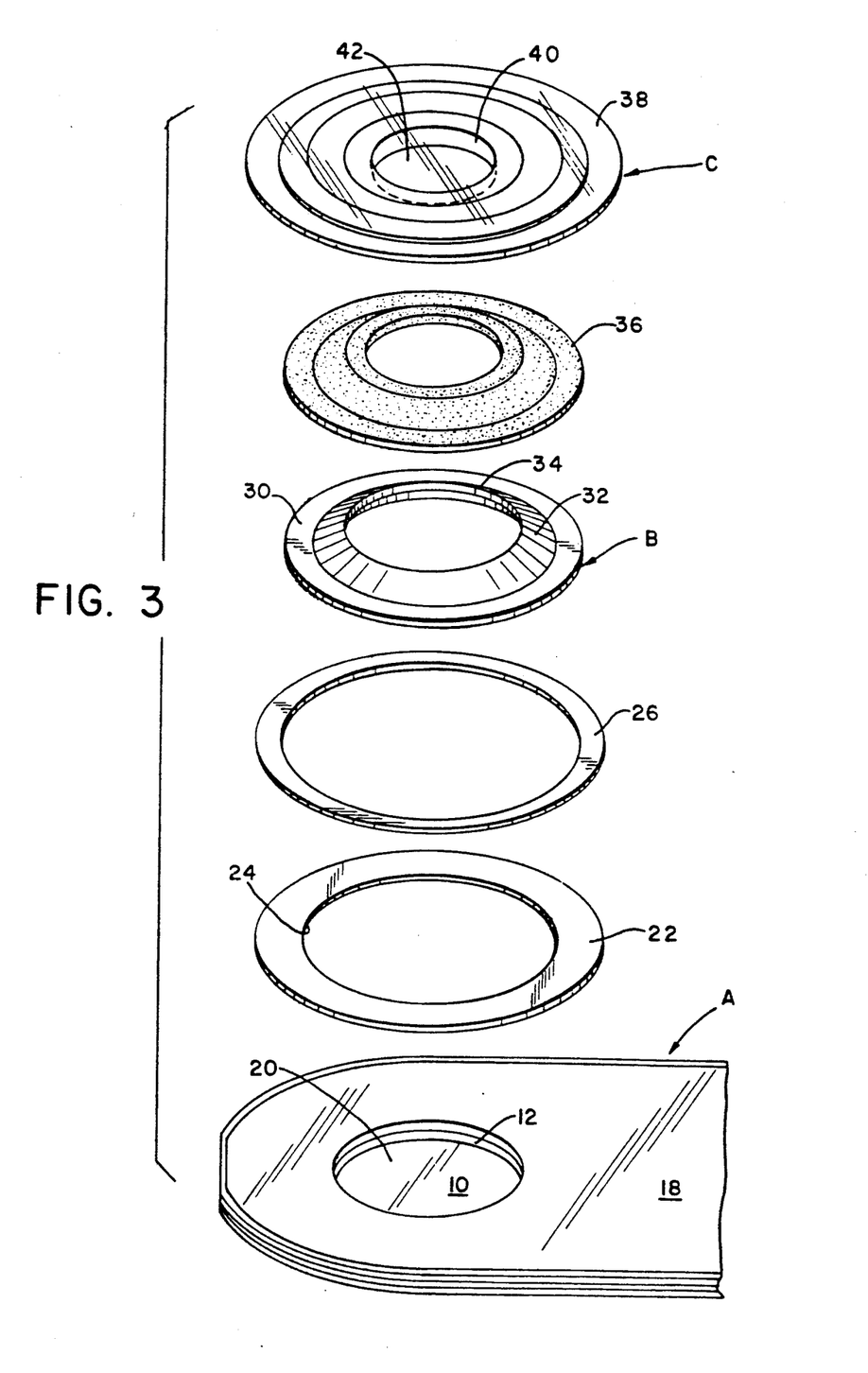
FIG. 3 is an exploded isometric view of the ostomy device of FIG. 1.

FIGS. 1, 2 and 3 illustrate a first preferred embodiment of an ostomy device which includes a pouch or bag, generally designated A, and an injection molded, substantially rigid or semi-rigid annular convex faceplate disk of the present invention, generally designated B. In this embodiment, a pouch A is permanently connected to disk B by heat welding. Disk B is preferably made of polyethylene, a polyethylene-ethylene vinyl acetate blend, or the like. Atop disk B is located a coating of adhesive which is protected from the environment during shipping and handling by a protective plastic shield, generally designated C.

Pouch A has a front wall 10 and a rear wall 12 made of thin, flexible film which is heat welded around the periphery 14 to form an enclosed receptacle. Depending upon the type of stomal discard, the pouch may include drainable outlet 16 which is sealed with a clip or it may include a liquid drainable top valve or the bottom merely be sealed in the same manner as periphery 14. In the embodiment shown in FIGS. 1, 2, and 3, disk B is heat welded to rear pouch wall 12 and then front pouch wall 10 is welded along the periphery 14 to form the completed pouch.

The films from which the pouch may be made are selected from materials which possess the properties of being moisture impermeable, odor impermeable and capable of being heat sealed or impulse welded. Suitable materials include polyethylene, co-polymers of polyethylene and ethylene vinyl acetate, co-polymers of vinyl chloride and polyvinylidene chloride and laminates thereof. The pouch walls are preferably from about two to four mils thick.

In some cases, it is desirable, in order to enhance the comfort of the patient, to use a flocking material for lining the exterior surface of pouch wall 12. Accordingly, a sheet of flocking material 18 is shown adjacent the surface of pouch wall 12. Flocking material 18 preferably has its smooth side outwards.

An inlet opening 20 is provided in rear pouch wall 12 and flocking sheet 18. A microporous collar 22 is situated adjacent the exposed surface of flocking sheet 18. Collar 22 has an opening 24 which is larger in diameter than inlet opening 20 on pouch A but is aligned therewith.

Collar 22 consists of a pressure sensitive adhesive layer and a backing. The adhesive layer can be an acrylic microporous adhesive as taught by Copeland in U.S. Pat. No. 3,121,021, a microporous hydrocolloid adhesive as taught by Cilento in U.S. Pat. No. 4,427,727, or a polyisobutylene-hydrocolloid containing adhesive as taught by Chen in U.S. Pat. No. 3,339,546, by Chen et al. in U.S. Pat. No. 4,192,785, by Pawelchak in U.S. Pat. No. 4,393,080, or it can be adhesive composition containing a styrene type block copolymer in addition to the polyisobutylene and hydrocolloids as taught by Doyle et al. in U.S. Pat. No. 4,551,490. The backing is a woven or non-woven fabric or a polymeric film. The fabric is employed particularly if the adhesive layer is microporous. Collar 22 is preferably from about 3 to about 15 mils in thickness.

Situated over collar 22 is a ring of silicone release paper 26. Paper 26 has an outer diameter which is approximately equal to the outer diameter of the microporous collar 22. However, the inner diameter of paper ring 26 is substantially larger than the inner diameter of the microporous collar 22. This configuration permits the release paper 26 to be removed from the surface of microporous collar 22 without interference from the convex disk B and at the same time permits the undersurface of convex disk B to be welded to pouch A forming an annular bond.

Convex disk B, has an undersurface which is substantially flat, as seen in FIG. 2, to facilitate welding to the pouch wall. The upper surface of collar B has a substantially planar peripheral portion 30 and a convex central portion 32 with a central opening 34 somewhat smaller than the inlet opening 20 in pouch A.

Situated on top of disk B is an adhesive wafer 36 which has a configuration precisely the same as the contour of the upper surface of disk B. Adhesive layer 36 can be any pressure sensitive adhesive suitable for use on human skin and capable of supporting the weight of the appliance. Preferably, the adhesive consists of a elastomeric substance such as polyisobutylene containing one or more hydrocolloids as taught by Chen in U.S. Pat. No. 3,339,546, by Chen et. al. in U.S. Pat. No. 4,192,785, by Pawelchak in U.S. Pat. No. 4,393,080 or it can additionally include a styrene type block copolymer as taught by Doyle et al. in U.S. Pat. No. 4,551,490. Adhesive layer 36 is preferably from about 20 to 70 mils thick.

Situated on top of adhesive layer 36 is a protective shield made of thermoplastic or thermosetting plastic such as styrene (available from Mead Products), an ionomer such as Surlyn (a plastic resin available from Du Pont) or the like, which is formed by the vacuum forming process described below. Shield C has a contour which is identical to the contour of the exterior surface of disk B but has an outer diameter which is larger than the outer diameter of disk B such that the peripheral portion 38 thereof also covers some or all of the release paper 26. The surface of shield C which contacts the adhesive is coated with a release agent such as silicone.

Unlike the release paper used on adhesive coated convex parts in the prior art, shield C has a contour which is virtually identical to the contour of the outer surface of disk B and is virtually wrinkle-free. It protects adhesive layer 36 from the environment, prevents localized drying of the adhesive and maintains a smooth, continuous adhesive surface to ensure patient comfort and a strong seal.

Figure 4:
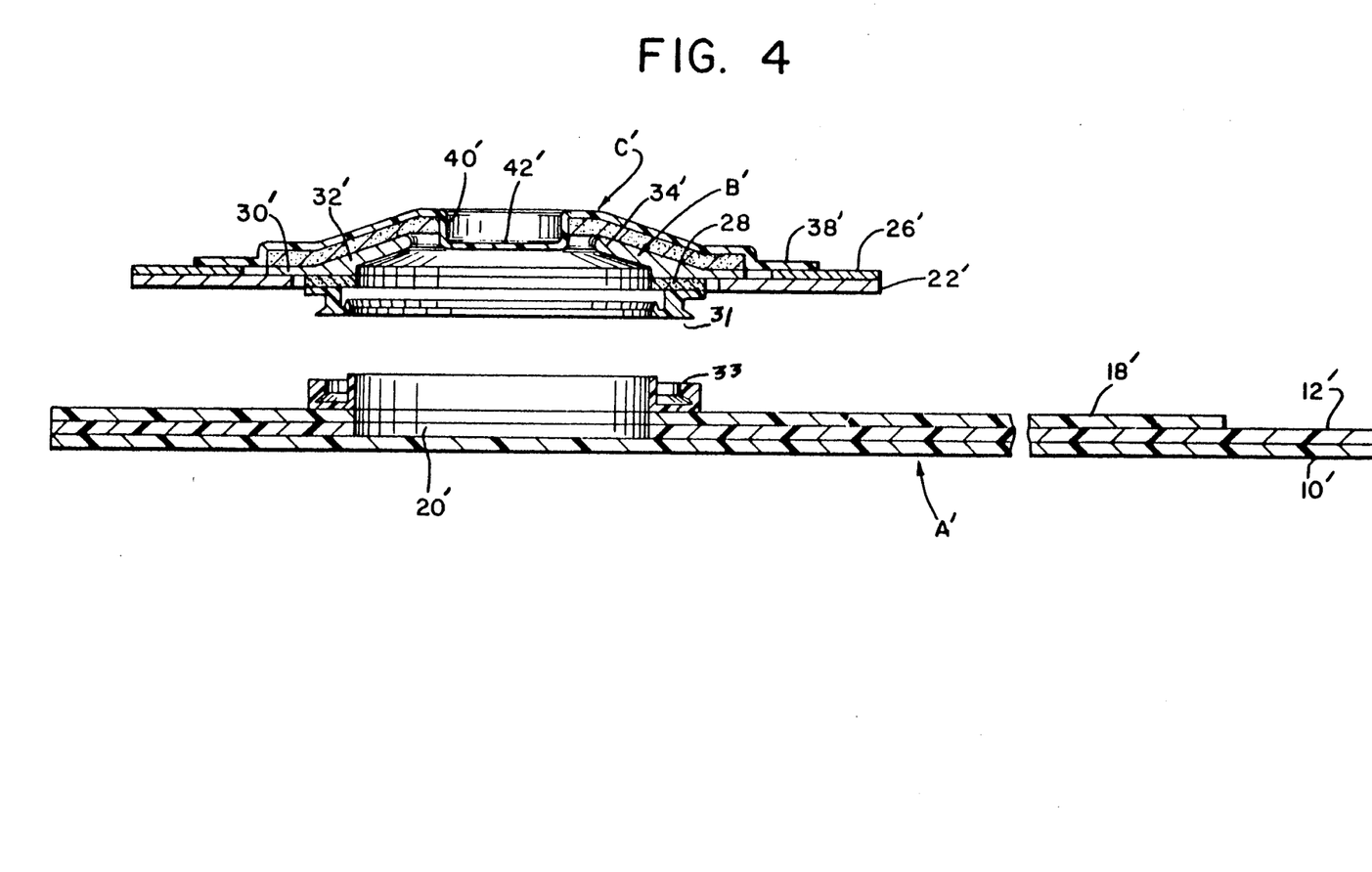
FIG. 4 is a cross-sectional view of a second preferred embodiment of an ostomy device including the faceplate of the present invention.

FIG. 4 illustrates another preferred embodiment of an ostomy device including the faceplate of the present invention. Unlike the first preferred embodiment in which pouch A is welded directly to disk B, in this embodiment, pouch A is detachably mounted to disk B. This two-piece device permits the pouch to be removed from the body without removal of the faceplate.

The parts of the ostomy device of FIG. 4 which are identical to those of the first preferred embodiment are denoted by a primed number. The only material difference between the embodiments is the inclusion of interengaging coupling rings between the disk and pouch in the second embodiment. In particular, FIG. 4 shows that disk B' is provided with a coupling ring 31 which is affixed to the underside of disk B' by a layer of adhesive 28' or other conventional method. Pouch A' is provided with a mating ring 33 affixed to wall 12 surrounding the stoma receiving opening 20. Rings 31 and 33 snap together to provide a fluid-tight seal between disk B' and pouch A'.

Figure 5:
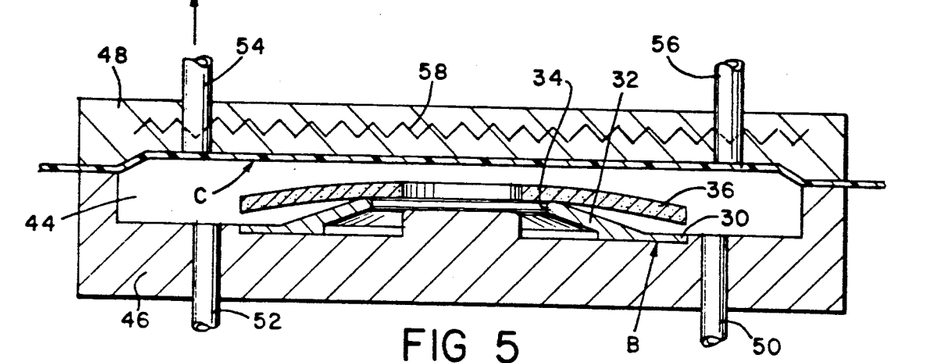
FIG. 5 is an idealized cross-sectional view of a vacuum forming chamber of the type used in the present invention showing the assembly during the first step in the vacuum forming process.
Figure 6:
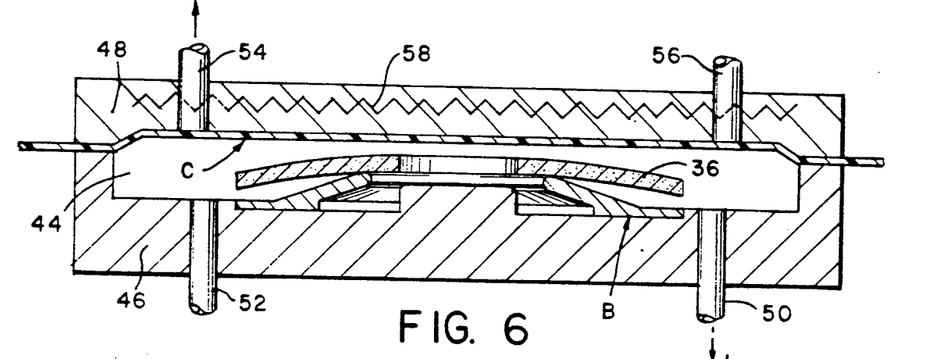
FIG. 6 is a view similar to FIG. 5, but showing the intermediate step in the vacuum forming process.
Figure 7:
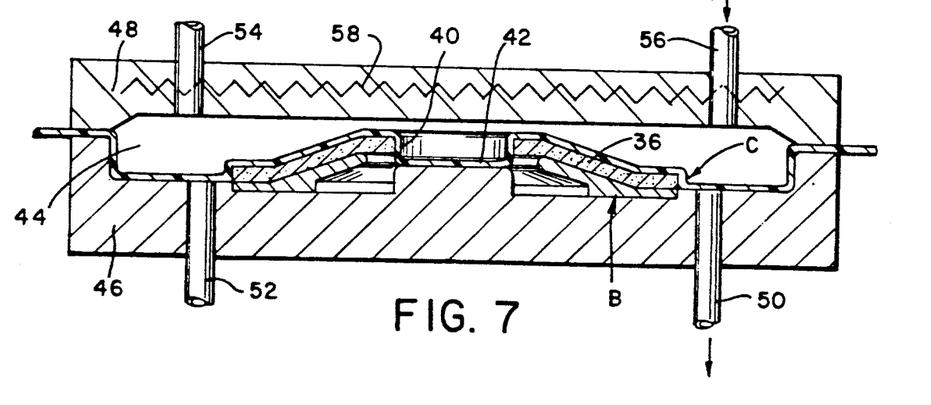
FIG. 7 is a view similar to FIG. 5 but showing the final step in the vacuum forming process of the present invention.

FIGS. 5, 6 and 7 schematically depict three of the steps in the vacuum forming process in which plastic shield C is formed over disk B and the air gaps in adhesive 36 are eliminated. Although these figures illustrate the process with a disk of the type employed in the first embodiment, it should be understood that the process is precisely the same when a disk of the type used in the second embodiment is utilized. These figures depict a chamber 44, preferably of circular configuration which is defined by a bottom portion 46 and a top portion 48 which are displacable relative to each other so as to open chamber 44 to permit the parts of the faceplate to be inserted and removed. The lower portion 46 and the upper portion 48 are each provided with a vacuum port and a vent port. In each case, the vacuum port is connected to a vacuum pump or the like of conventional design and the vent port is provided with a valve, which may be a solinoid operated valve or the like, for venting to the atmosphere.

More specifically, the bottom portion 46 of the chamber has a vacuum port 50 and a vent port 52. Similarly, top portion 48 has a vacuum port 54 and a vent port 56. In addition, upper portion 48 is preferably provided with an electric heating coil 58. However, portion 48 can be heated by other means if desired.

At the beginning of the process, portions 46 and 48 are displaced from each other such that chamber 44 is opened. A disk B is placed within the cavity, nesting in an indentation on the upper surface of portion 46. On top of disk B is situated an annular adhesive wafer 36 which is positioned such that the outer periphery thereof is substantially aligned with the outer periphery of disk B. Wafer 36 is in a substantially planar condition at this stage. A thin planar sheet of plastic, which will form shield C, is placed over the bottom portion 46 of the chamber and extends outwardly beyond the cavity. This sheet separates the cavity into upper and lower sections. Portions 46 and 48 are then closed such that chamber 44 is sealed.

First, the upper portion 48 of the chamber is heated by means of coil 58. Then, the upper section of the cavity is evacuated by connecting port 54 to a vacuum pump. This creates a vacuum between the lower surface of portion 48 and the upper surface of the sheet so as to draw the sheet against the heated roof of the chamber. As the plastic sheet C is heated it becomes softened and thereafter conforms to the contour of the upper surface of the chamber, as shown in FIG. 5.

Port 50 in section 48 of the vacuum chamber is then connected to the vacuum pump and the remainder, that is the lower portion of chamber 44, is evacuated. This will cause all of the air between disk B and adhesive wafer 36 and between wafer 36 and shield C to be drawn out. The assembly now appears as shown in FIG. 6.

The next step is to open the vent port 56 in section 48 of the chamber such that softened shield C is pressed over disk B. This wafer 36 to conform to the contours of the upper surface of disk B and, similarly, the softened shield C to conform exactly to the contours of the wafer 36 and hence the outer surface of disk B, as shown in FIG. 6. When this occurs, substantially all of the gaps between disk B and shield C are eliminated.

A perfectly fitting protective shield, without any gaps or wrinkles, is formed. Shield C is permitted to cool such that it retains its shape. The vacuum pump is disconnected from port 50 and vent port 52 is opened such that the assembly can be removed from the chamber and moved along the assembly line, by the web formed of the plastic sheet, to a cutting apparatus which separates the faceplate from the web.

After the assembly is formed as described above, it is heat or impulse welded to the pouch along annular section 28. Preferably, fabric collar 22 is affixed to the rear of the disk outside area 28. If the disk is designed for use as a part of a two-part device, the coupling ring is already in place and the procedure of welding to the pouch is not required. The process eliminates air gaps or pockets left in the adhesive which permit localized drying. Moreover, the contours of the shield will be smooth and wrinkle-free as will the adhesive layer surface, such that a firm seal can be obtained with the skin surrounding the stoma.

Figure 8:
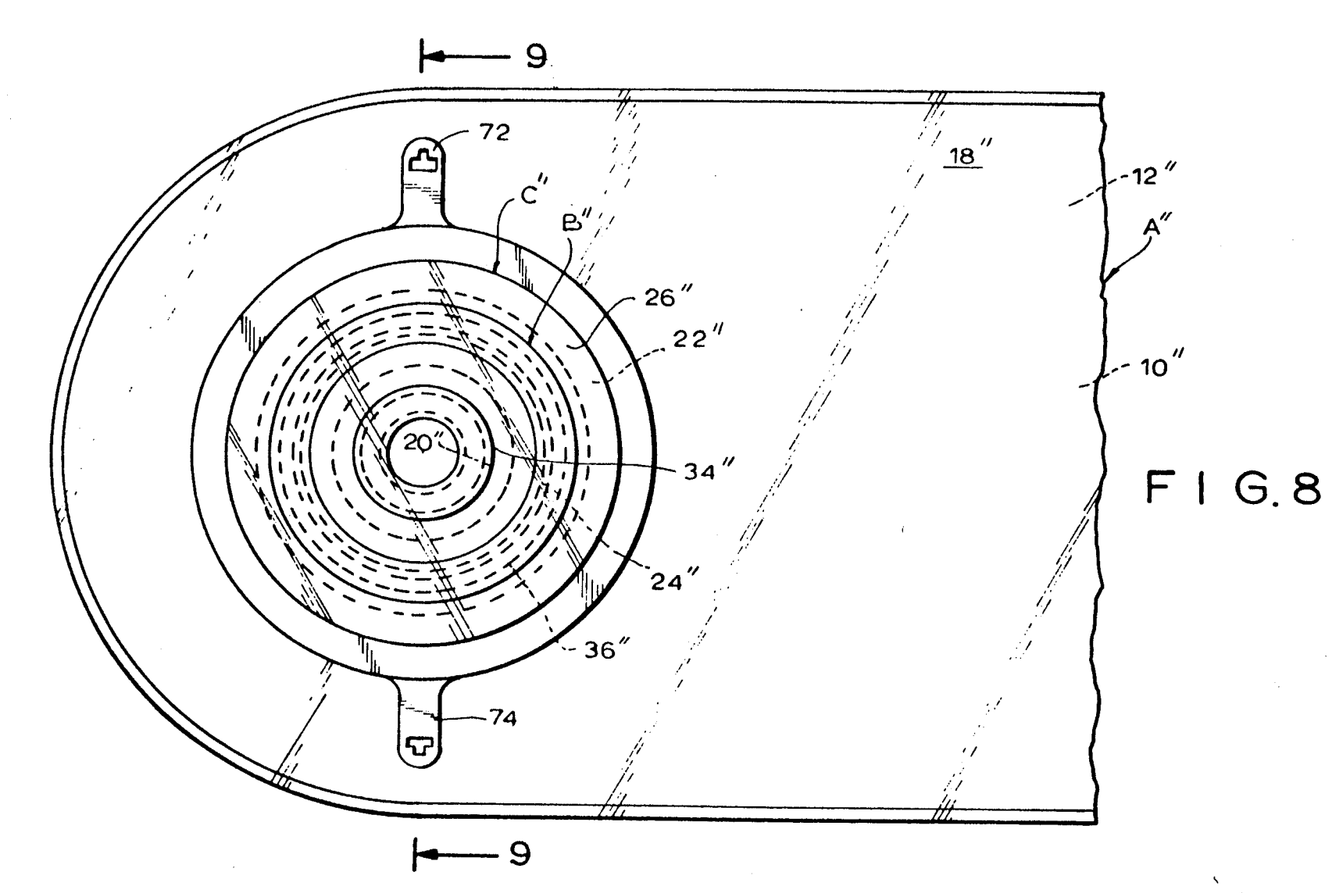
FIG. 8 is a plan view of third preferred embodiment of the present invention which includes a belt ring.
Figure 9:
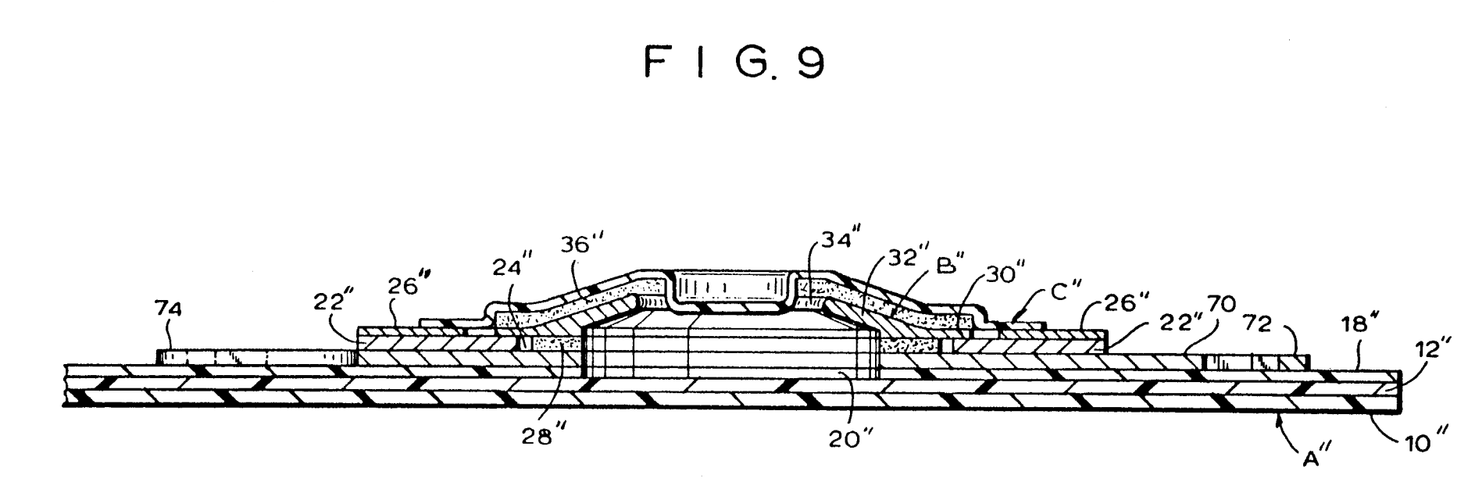
FIG. 9 is a cross-sectional view taken along line 9—9 of FIG. 8.

FIG. 8 and 9 illustrate still another preferred embodiment of an ostomy device including the faceplate of the present invention. Unlike the first embodiment, in this embodiment pouch A" is provided with an annular ring 70 secured to the rear pouch wall. The ring includes lugs 72, 74 for the attachment of a security belt (not shown). The substantially flat surface of disk B" is then secured to the annular ring 70. This can be done adhesively by means of a double sided adhesive disk, by coating the flat surface of disk B" or the surface of annular ring 70 with a liquid hot melt adhesive 28".

Another bonding technique employs locating a temperature controlled plate between the annular ring and the flat surface of disk B" for a measured period of time as ring 70 and disk B" are pushed to the plate. The plate can be made so only the section that is in the weld area is heated. This heated area is covered with a release coating to keep the hot plastic from sticking to it. The plate is removed when the flat surface of disk B" and annular ring 70 reach the welding temperature. The pouch and disk B" are then pressed together to form the welded unit. In this embodiment, annular ring 70 and disk B" are preferably formed of a blend of polyethylene and ethylene vinyl acetate.

Figure 10:
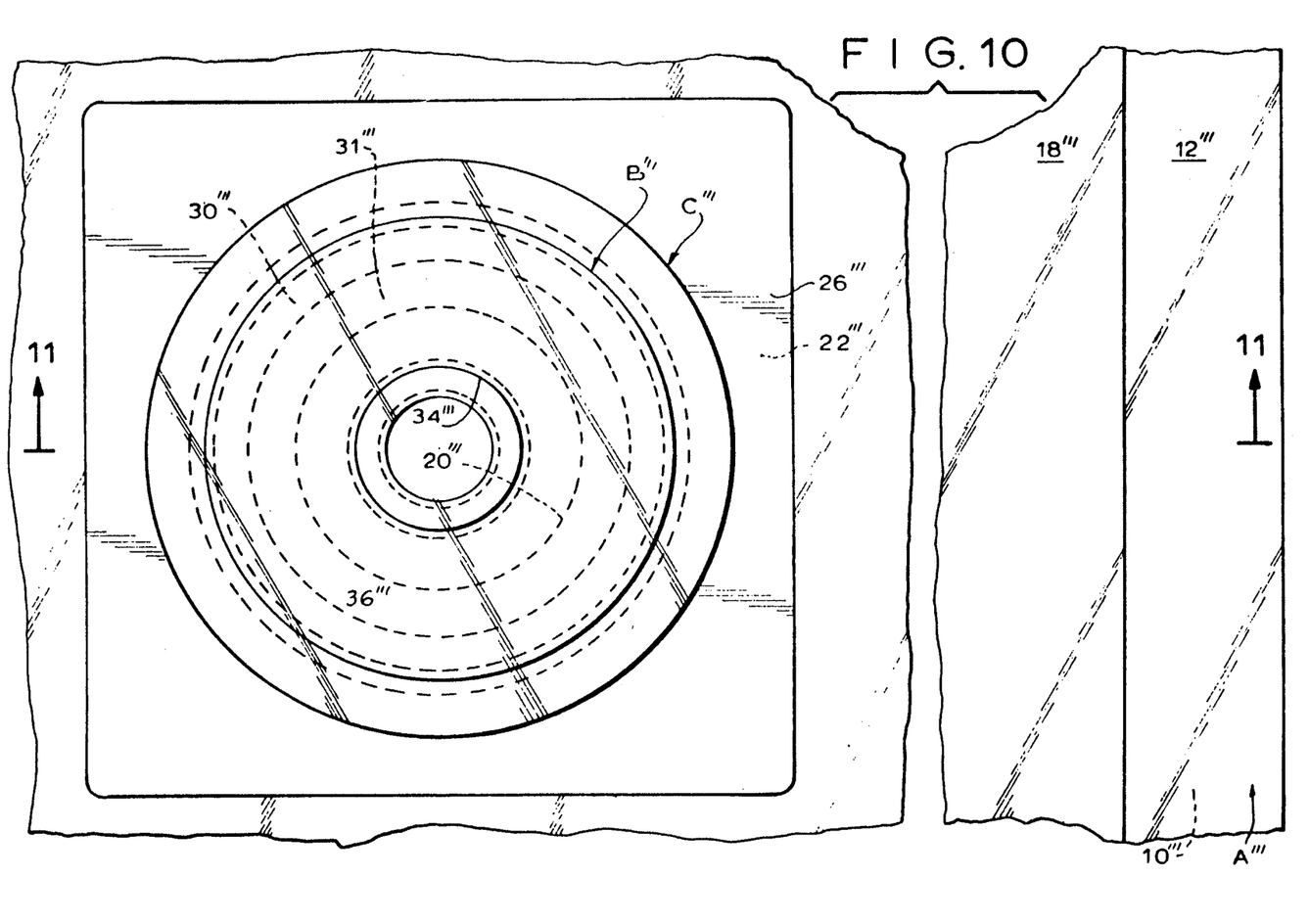
FIG. 10 is a plan view of a fourth preferred embodiment of the present invention which is a two piece device where the faceplate coupling ring is bonded to the convex disk.
Figure 11:
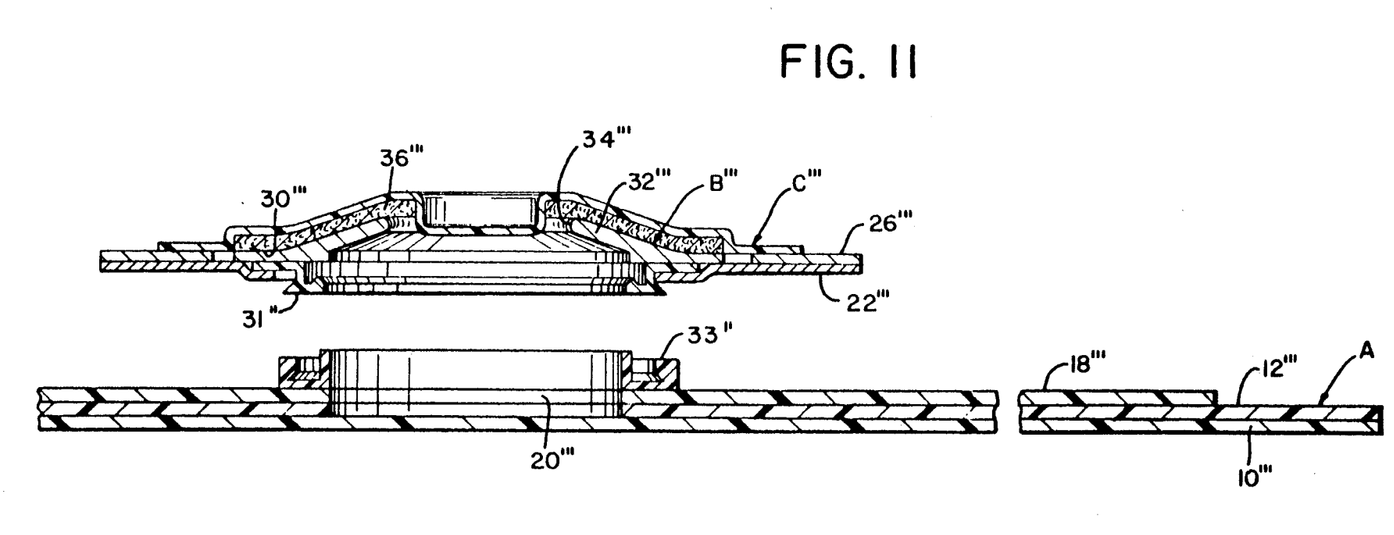
FIG. 11 is a cross sectional view taken along line 11—11 of FIG. 10.

FIGS. 10 and 11 illustrate another preferred embodiment of the present invention which is similar to the embodiment showing in FIG. 4 in that its includes a two piece device where the faceplate has a coupling ring attached thereto. However, in this embodiment, coupling ring 31'" is affixed directly to the planar under surface of disk B'". This structure can be achieved in one of two ways. Coupling ring 31'" can be affixed to disk B'" after the wafer 36'" and protective shield C'" have been vacuum formed thereon by adhesive, ultra sonic welding or spin welding. Thus, the faceplate assembly is first formed as shown in FIGS. 5, 6, and 7 and thereafter affixed to a pouch, as illustrated in FIG. 2, to coupling ring 31" by adhesive as illustrated in FIG. 4 or directly to coupling ring 31'" as illustrated in FIG. 9, depending on the desired structure of the resulting product.

Alternatively, coupling ring 31'" may be bonded by adhesive or welding, to disk B'" prior to being placed in the vacuum chamber. The assembly is then processed as before and the end product includes a faceplate with the coupling ring directly attached as illustrated in FIG. 11.

It should now be appreciated that the present invention relates to a convex adhesive faceplate with a plastic protective shield for use in both one-piece and two-piece ostomy devices, as well as a method for fabricating same. The method includes a vacuum forming process which is adaptable to use in mass production and which ensures that gaps are eliminated preventing localized drying of the adhesive and at the same time results in a shield with a smooth, wrinkle-free surface, the contour of which is virtually identical to the upper surface of the convex disk. When the shield is removed, the adhesive layer will be completely smooth, continuous and uniform and, hence, capable of forming an excellent seal with the skin surrounding the stoma.

While only a limited number of preferred embodiments of the present invention has been disclosed for purposes of illustration, it is obvious that many variations and modifications could be made thereto. It is intended to cover all these variations and modifications which fall within the scope of the present invention as defined by the following claims:

We claim:

1. A method for fabricating a faceplate for an ostomy device of the type including a collection pouch having an inlet and being designed to be affixed to the body by the faceplate, the method comprising the steps of: forming an annular disk having a planar peripheral portion and a convex central portion with a central opening, placing the disk within a vacuum chamber, placing a substantially planar wafer of adhesive adjacent one side of the disk, placing a substantially planar sheet of plastic to form a shield adjacent the wafer so as to separate the chamber into first and second portions, evacuating the first portion of the chamber to draw the sheet against a surface of the chamber, heating said surface to soften the plastic sheet, evacuating the second portion of the chamber to remove substantially all of the air between the disk and sheet, releasing the vacuum in the first portion of the chamber to press the softened plastic sheet against the wafer and toward the disk, said shield having a substantially wrinkle-free surface, with a contour substantially identical to the contour of the disk, the faceplate being adapted to thereafter be connected to the collection pouch such that the inlet aligns with the central opening of the disk.

2. The method of claim 1, where said surface of said chamber is electrically heated.

3. The method of claim 1, where said shield is substantially circular.

4. The method of claim 1, where said shield has a larger outer diameter than said disk.

5. The method of claim 1, further comprising the step of affixing a coupling ring to the disk.

6. The method of claim 5 wherein the step of affixing the coupling ring to the disk takes place before the disk is placed in the chamber.

7. The method of claim 5 wherein the step of affixing the coupling ring to the disk takes place after the assembly is removed from the chamber.

8. The method of claim 1, wherein the step of forming the disk includes the step of affixing safety belt engaging means to the disk.

* * * * *